(12) United States Patent
Mergelsberg et al.

(10) Patent No.: US 7,459,556 B2
(45) Date of Patent: Dec. 2, 2008

(54) PROCESS FOR PREPARING SUBSTITUTED 8-AZABICYCLO[3.2.1]OCTAN-3-OLS

(75) Inventors: Ingrid Mergelsberg, Watchung, NJ (US); Gerald Werne, Kriens (CH)

(73) Assignee: Schering-Plough Ltd., Lucerne (CH)

( * ) Notice: Subject to any disclaimer, the term of this patent is extended or adjusted under 35 U.S.C. 154(b) by 392 days.

(21) Appl. No.: 11/225,244

(22) Filed: Sep. 13, 2005

(65) Prior Publication Data

US 2006/0058343 A1  Mar. 16, 2006

Related U.S. Application Data

(60) Provisional application No. 60/610,151, filed on Sep. 15, 2004.

(51) Int. Cl.
| C07D 239/02 | (2006.01) |
| C07D 451/02 | (2006.01) |
| C07D 401/00 | (2006.01) |
| C07D 405/00 | (2006.01) |
| C07D 409/00 | (2006.01) |
| C07D 411/00 | (2006.01) |
| C07D 413/00 | (2006.01) |
| C07D 417/00 | (2006.01) |

(52) U.S. Cl. ............... 544/335; 546/124; 546/125; 546/126; 546/127

(58) Field of Classification Search ............ 546/124, 546/125, 126, 127; 544/335
See application file for complete search history.

(56) References Cited

U.S. PATENT DOCUMENTS

| 2,921,938 A * | 1/1960 | Wetteray et al. ............ 546/129 |
| 6,262,066 B1 | 7/2001 | Tulshian et al. |
| 6,722,254 B1 | 4/2004 | Davies |
| 2003/0119847 A1 * | 6/2003 | Tulshian et al. ....... 514/252.18 |

FOREIGN PATENT DOCUMENTS

WO  WO 02/085900  10/2002

OTHER PUBLICATIONS

Cope et al., Journal of the American Chemical Society, 1951, vol. 73, pp. 3419-3424.*
Novelli. F., et al., "Sptro[1,2,4-benzotriazine-3(4H),4'-(1'-substituted)piperldines] and related compounds as ligands for sigma receptors", II Farmaco, 57. 2002. pp. 871-882.
Nielsen, Simon Feldbaek, et al., "Novel Potent Ligands for the Central Nicotinic Acetylcholine Receptor. Synthesis, Receptor Binding, and 3D-QSAR Analysis", J. Med. Chem., 43, 2000, pp. 2217-2226.
Olivo, Horaclo F., et al., "Syntheses of New Open-Ring and homo-Epibatidine Analogues from Tropinone", J. Org. Chem., 64, 1999, pp. 4966-4988.
International Search Report, International Application No. PCT/US2005/032512, Date of Mailing: Jul. 19, 2005.

\* cited by examiner

*Primary Examiner*—D. Margaret Seaman
*Assistant Examiner*—Niloofar Rahmani
(74) *Attorney, Agent, or Firm*—Patent Practitioners of Schering Corporation

(57) ABSTRACT

The present invention relates to a process for preparing substituted 8-azabicyclo[3.2.1]octan-3-ols having the structural formula I

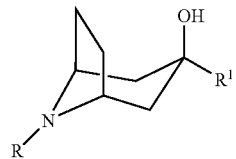

I or a pharmaceutically acceptable salt or solvate thereof, wherein R is benzyl, $R^5$-benzyl, allyl, —C(O)$R^6$, —C(O)OR$^8$ or —CH($R^7$)$_2$;
$R^1$ is optionally substituted aryl or optionally substituted heteroaryl; and
$R^5$, $R^6$, $R^7$ and $R^8$ are as defined in the specification;
comprising
a) reacting an amine of formula II

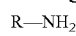

R—NH$_2$  II with 2,5-dimethoxytetrahydrofuran or HC(O)(CH$_2$)$_2$C(O)H, and C(O)(CH$_2$C(O)OR$^4$)$_2$, wherein $R^4$ is H or alkyl, to obtain a compound of formula III

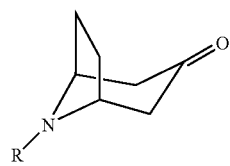

III b) reacting a compound of formula III with I-R$^1$, alkyl lithium, and optionally a lithium salt, to obtain a compound of formula I; and
c) optionally converting a compound of formula I wherein R is benzyl, $R^5$-benzyl, allyl, —C(O)$R^6$ or —C(O)OR$^8$ to a compound of formula I wherein R is —CH($R^7$)$_2$. Intermediates in the process are also claimed.

13 Claims, No Drawings

PROCESS FOR PREPARING SUBSTITUTED 8-AZABICYCLO[3.2.1]OCTAN-3-OLS

CROSS REFERENCE TO RELATED APPLICATION

This application claims the benefit of U.S. Provisional Application No. 60/610,151, filed Sep. 15, 2004.

FIELD OF THE INVENTION

The present invention relates to a process for preparing substituted 8-azabicyclo[3.2.1]octan-3-ols.

BACKGROUND

Substituted 8-azabicyclo[3.2.1]octan-3-ol compounds disclosed in U.S. Pat. No. 6,262,066 are NOP receptor agonists (previously known as ORL-1 receptor agonists) useful in the treatment of various disorders such as pain, anxiety and cough. U.S. Pat. No. 6,262,066 discloses a process for preparing the claimed compounds comprising an expensive and unstable tropinone as a starting material.

A preferred group of 8-azabicyclo[3.2.1]octan-3-ols, including 8-[bis(2-chlorophenyl)methyl]-3-pyrimidin-2-yl-8-azabicyclo[3.2.1]octan-3-ol, is specifically disclosed in U.S. Pat. No. 6,727,254. The multi-step process disclosed in U.S. Pat. No. 6,727,254 comprises reaction of a tropinone with a diphenylmethyl derivative, followed by reaction with a tributyltin derivative of pyrimidine and an alkyl lithium derivative.

SUMMARY OF THE INVENTION

The present invention relates to a process for preparing compounds having the structural formula I

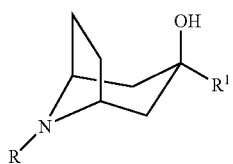

I or a pharmaceutically acceptable salt or solvate thereof, wherein

R is benzyl, $R^5$-benzyl, allyl, —C(O)$R^6$, —C(O)O$R^8$ or —CH($R^7$)$_2$;

each $R^7$ is independently selected from the group consisting of $R^2$-phenyl and $R^2$-heteroaryl;

$R^1$ is $R^3$-aryl, $R^3$-heteroaryl, $R^3$-arylalkyl or $R^3$-heteroarylalkyl;

$R^2$ is 1 to 3 substituents independently selected from the group consisting of hydrogen, halogen, alkyl, hydroxy and alkoxy;

$R^3$ is 1-3 substituents independently selected from the group consisting of hydrogen, halogen and alkyl;

$R^5$ is 1 or 2 substituents independently selected from the group consisting of halogen, alkoxy and —NO$_2$;

$R^6$ is H, alkyl, haloalkyl or benzyl; and $R^8$ is alkyl, benzyl or allyl;

comprising
 a) reacting an amine of formula II

II wherein R is as defined above, with 2,5-dimethoxytetrahydrofuran or HC(O)(CH$_2$)$_2$C(O)H, and with C(O)(CH$_2$C(O)O$R^4$)$_2$, wherein $R^4$ is H or alkyl, in a buffer, optionally in the presence of a base, to obtain a compound of formula III

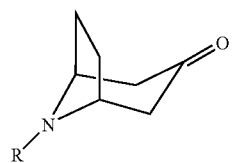

III b) reacting a compound of formula III with I-$R^1$, wherein $R^1$ is as defined above, with alkyl lithium, optionally in the presence of a lithium salt, to obtain a compound of formula I;
 c) optionally converting a compound of formula I wherein R is benzyl, $R^5$-benzyl, allyl, —C(O)$R^6$ or —C(O)O$R^8$ to a compound of formula I wherein R is —CH($R^7$)$_2$ by
  i) removing the benzyl, $R^5$-benzyl, allyl, —C(O)$R^6$ or —C(O)O$R^8$ group to obtain a compound of formula I(c)(i)

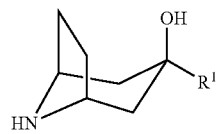

I(c)(i)

and
  ii) reacting the compound of I(c)(i) or a salt thereof with a compound of formula IV

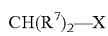

IV wherein X is halogen, —OSO$_2$CH$_3$ or —O-(p-toluenesulfonyl); and
 d) optionally recrystallizing the product of step b) or step c) to obtain a purified product.

Also claimed are novel intermediates of formula Ib' and I(c)(i)

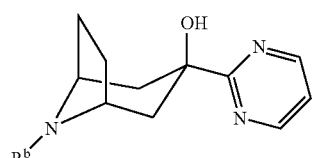

Ib'

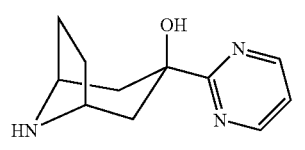

I(c)(i)' wherein $R^b$ is benzyl, $R^5$-benzyl, allyl, —C(O)$R^6$ or —C(O)O$R^8$.

Also claimed is a method for preparing a compound of formula V

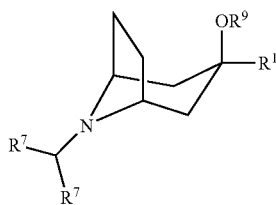

V wherein $R^9$ is alkyl and $R^1$ and $R^7$ are as defined above for formula I, provided that $R^2$ is not hydroxy, comprising alkylating a compound of the formula VI

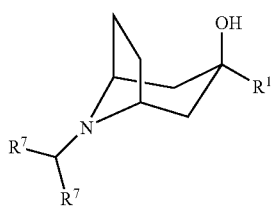

VI i.e., the product of step (c).

It is further contemplated that this process would be useful for preparing a compound wherein R is any of the $Z^1$, $Z^2$ and $Z^3$ groups disclosed in U.S. Pat. No. 6,262,066, incorporated herein by reference.

DETAILED DESCRIPTION

In one embodiment, the process of the invention comprises preparing a compound of formula Ia

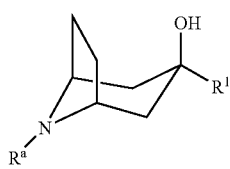

Ia wherein $R^a$ is —$CH(R^7)_2$, preferably

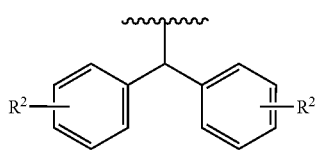

wherein each $R^2$ is independently selected from the group consisting of hydrogen, halogen, alkyl, hydroxy and alkoxy;

$R^1$ is $R^3$-aryl, $R^3$-heteroaryl, $R^3$-arylalkyl or $R^3$-heteroaryl alkyl, wherein $R^3$ is 1-3 substituents independently selected from the group consisting of hydrogen, halogen and alkyl;

comprising a) reacting an amine of formula IIa

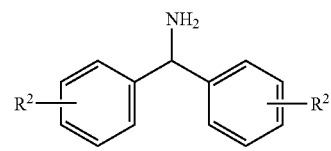

IIa $CH(R^7)_2$—$NH_2$ preferably

IIa' with 2,5-dimethoxytetrahydrofuran or $HC(O)(CH_2)_2C(O)H$, and with $C(O)(CH_2C(O)OR^4)_2$, wherein $R^4$ is H or alkyl, in a buffer, optionally in the presence of a base, to obtain a compound of formula IIIa

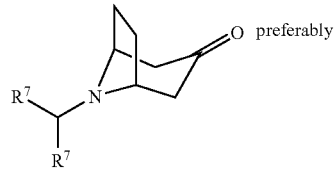

IIIa preferably

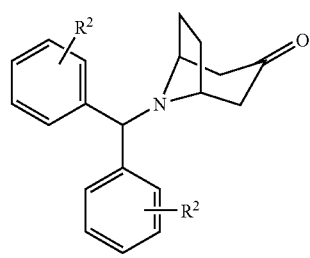

IIIa' b) reacting a compound of formula IIIa with I-$R^1$, wherein $R^1$ is as defined above, with alkyl lithium, optionally in the presence of a lithium salt, to obtain a compound of formula Ia; and optionally recrystallizing the product of step b) to obtain a purified product.

In preferred embodiment, the process of the invention comprises preparing a compound of formula Ia'

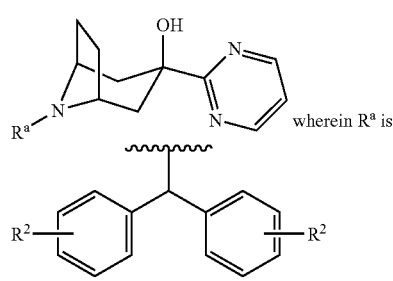

Ia' wherein $R^a$ is wherein $R^2$ is 1 to 3 substituents independently selected from the group consisting of hydrogen, halogen, alkyl, hydroxy and alkoxy;

comprising
a) reacting an amine of formula IIa

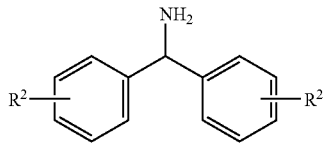
IIa' with 2,5-dimethoxytetrahydrofuran and C(O)(CH$_2$C(O)OR$^4$)$_2$, wherein R$^4$ is H, in a buffer, optionally in the presence of a base, to obtain a compound of formula IIIa'

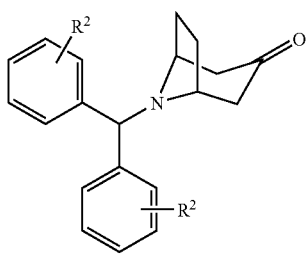
IIIa' b) reacting a compound of formula IIIa' with 2-iodopyrimidine, n-butyl lithium and LiBr to obtain a compound of formula Ia'; and
optionally recrystallizing the product of step b) to obtain a purified product.

In a second embodiment, the process of the invention comprises preparing compounds of formula Ia

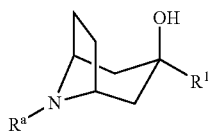
Ia wherein R$^a$ is —CH(R$^7$)$_2$, preferably

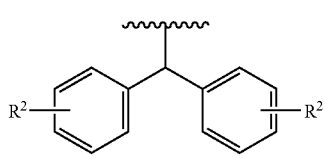

wherein each R$^2$ is independently selected from the group consisting of hydrogen, halogen, alkyl, hydroxy and alkoxy;
R$^1$ is R$^3$-aryl, R$^3$-heteroaryl, R$^3$-arylalkyl or R$^3$-heteroarylalkyl, wherein R$^3$ is 1-3 substituents independently selected from the group consisting of hydrogen, halogen and alkyl;
comprising
a) reacting an amine of formula IIb R$^b$—NH$_2$   IIb wherein R$^b$ is benzyl, R$^5$-benzyl, allyl, —C(O)R$^6$ or —C(O)OR$^8$, with 2,5-dimethoxytetrahydrofuran or HC(O)(CH$_2$)$_2$C(O)H, and with C(O)(CH$_2$C(O)OR$^4$)$_2$, wherein R$^4$ is H or alkyl, in a buffer, optionally in the presence of a base to obtain a compound of formula IIIb

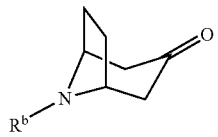
IIIb b) reacting a compound of formula IIIb with I-R$^1$, wherein R$^1$ is as defined above, with alkyl lithium, optionally in the presence of a lithium salt, to obtain a compound of formula Ib

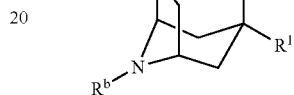
Ib wherein R$^b$ is as define above;
c) converting the compound of formula Ib to a compound of formula Ia wherein R$^a$ is —CH(R$^7$)$_2$, preferably

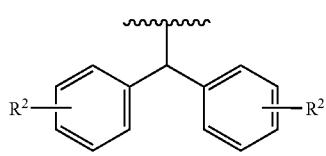

by
i) removing the benzyl, R$^5$-benzyl, allyl, —C(O)R$^6$ or —C(O)OR$^8$ group to obtain a compound of formula I(c)(i)

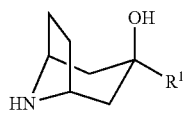
I(c)(i)

and
ii) reacting the compound of I(c)(i) or a salt thereof with a compound of formula IV CH(R$^7$)$_2$—X preferably   IV

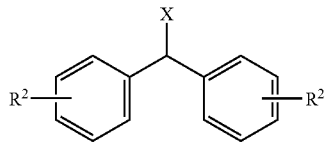
IV' wherein X is halogen, —OSO$_2$CH$_3$ or —O-(p-toluenesulfonyl); and d) optionally recrystallizing the product of step c) to obtain a purified product.

In a preferred embodiment, the process of the invention comprises preparing compounds of formula Ia'

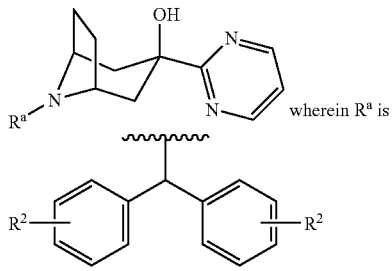

wherein R² is 1 to 3 substituents independently selected from the group consisting of hydrogen, halogen, alkyl, hydroxy and alkoxy;

comprising a) reacting an amine of formula IIb

wherein $R^b$ is benzyl, $R^5$-benzyl, allyl, —C(O)R⁶ or —C(O)OR⁸, wherein R⁸ is preferably tert-butyl or benzyl, with 2,5-dimethoxytetrahydrofuran or HC(O)(CH₂)₂C(O)H, and with C(O)(CH₂C(O)OR⁴)₂, wherein R⁴ is H or alkyl, in a buffer, optionally in the presence of a base to obtain a compound of formula IIIb

b) reacting a compound of formula IIIb with 2-iodopyrimidine, n-butyl lithium and LiBr to obtain a compound of formula Ib"

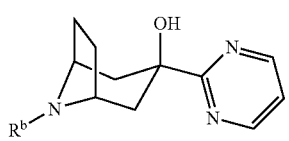

wherein $R^b$ is as defined above;

c) converting the compound of formula Ib" to a compound of formula Ia' wherein $R^a$ is

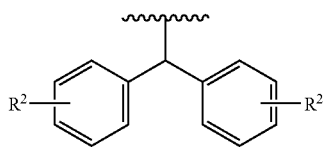

by i) removing the benzyl, $R^5$-benzyl, allyl, —C(O)R⁶ or —C(O)OR⁸ group to obtain a compound of formula I(c)(i)'

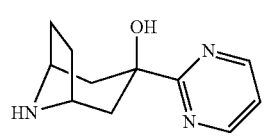

ii) reacting the compound of formula I(c)(i)' or a salt thereof with a compound of formula IV'

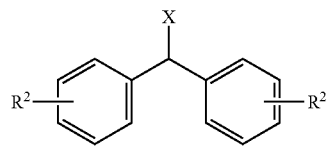

wherein X is halogen, —OSO₂CH₃ or —O-(p-toluenesulfonyl); and d) optionally recrystallizing the product of step c) to obtain a purified product.

Preferred compounds of formula I prepared by the claimed process are those wherein R is

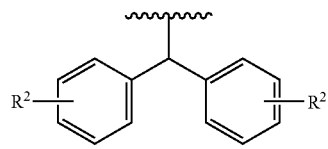

wherein each R² is halogen, more preferably chloro, still more preferably 2-chloro, and wherein R¹ is R³-heteroaryl, especially pyrimidyl, and more especially 2-pyrimidyl.

In particular, a preferred compound prepared by the claimed process has the structure I-A:

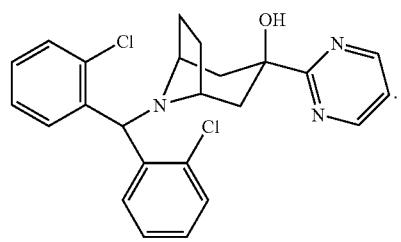

Compared to the previously disclosed procedures for making substituted 8-azabicyclo[3.2.1]octan-3-ols, the present process eliminates the use of nortropinone hydrochloride, an expensive and relatively unstable reagent.

Step (b) of the present process, comprising the addition of an alkyl lithium to a mixture of the tropinone of formula III and the iodo-heteroaryl, IR¹, is a one-step procedure resulting in high yields of the compound of formula I in excellent purity. This process eliminates the undesirable tin chemistry used in U.S. Pat. No. 6,727,254, as well as eliminating the isolation step and difficult work-up.

The preparation of the tropinone uses the known Robinson Schoepf synthesis, but for the preferred process of the invention, the successful addition to the ketone of an in situ formed 2-pyrimidyl anion, known in the literature to be unstable, is unexpected.

The present process is easier to perform than the procedures in the art, and provides the product in higher yield.

Starting materials of formula II are known in the art or can be prepared by procedures known in the art. For example, compounds of formula II wherein R is substituted diphenylmethyl can be prepared from the corresponding bromo derivative by reaction with ammonia gas in acetonitrile. The bromo derivative, in turn can be prepared using a Grignard reagent as described in Preparation 1, below.

In step (a), the reaction is carried out in a solvent and a buffer. The solvent is water or a water miscible organic solvent such as N-methylpyrrolidine (NMP), dimethylformamide (DMF), tetrahydrofuran (THF), acetonitrile, or an alcohol such as isopropanol, or a mixture thereof, optionally in the presence of a base such as NaOH (aqueous solution), triethylamine ($Et_3N$) or $NaHCO_3$. The buffer is an aqueous buffer wherein the buffering agent is, for example sodium acetate, sodium citrate or disodium hydrogenphosphate and the pH is acidified with an acid such as HCl, preferably to a pH of about 2 to about 6.

The reaction is carried out over a temperature of about 0° C. to about 60° C., most preferably starting at about 0-5° C., then increasing gradually to about 50° C.

The concentration of reactants in step (a) can vary in a range of about +/−20%. The amount of 2,5-dimethoxytetrahydrofuran can range from 1.1 to 1.35 equivalents and the amount of acetone dicarboxylic acid (or ester thereof) or $HC(O)(CH_2)_2C(O)H$ can vary from 1.1 to 2 equivalents; the amount of HCl can vary from 0.1 to 1.5 equivalents, and the amount of sodium acetate or other buffering agent can vary from 1 to 4 equivalents.

In step (b), the reaction is carried out in a solvent such as THF, toluene, DME, THF/n-hexane, THF/n-heptane or a mixture thereof. The concentration can vary from about 10× solvent to 30× solvent, with the concentration of $I-R^1$ being 1 to 5 equivalents, preferably 1 to 2 equivalents.

The reaction is carried out in a temperature range of about −20° C. to about −100° C., preferably at about −60° C. to about −100° C.

The alkyl lithium is, for example n-butyl lithium, sec butyl lithium, tert. butyl lithium or n-hexyl lithium, present in a range of 1 to 2.5 equivalents. N-hexyl lithium has the advantage of not generating a gas when the reaction is quenched. The alkyl lithium can be added as the last reagent, or it can be added simultaneously with $I-R^1$.

The lithium salt is, for example, LiBr, LiCl, lithium acetate or lithium tosylate. The concentration of lithium salt can vary from 0 equivalents to about 5 equivalents; preferably, it is present in a concentration of about 2.5 equivalents. The presence of the lithium salt improves the yield and purity of the product. For preparation of compounds wherein $R^1$ is pyrimidyl, the addition of the lithium salt increases the stability of the lithium pyrimidine species generated in situ by the addition of alkyl lithium to the iodopyrimidine. When used in the reaction, the lithium salt is added to $I-R^1$ before the alkyl lithium.

In step (c)(i), the conversion of a compound wherein R is benzyl, $R^5$-benzyl, allyl, $-C(O)R^6$ or $-C(O)OR^8$ to a compound wherein R is $-CH(R^7)_2$ is achieved by removing the nitrogen protecting group to obtain a compound of formula I(c)(i) or a salt thereof, using methods well known in the art. For example, the R group can be removed by reaction with a palladium catalyst. Typical procedures include hydrogenation with palladium on charcoal or reaction with tetrakis (triphenyl-phosphine)palladium, preferably in the presence of N,N-dimethyl barbituric acid. When a salt is of formula I(c)(i) is desired, e.g., an HCl or N,N-dimethyl barbituric salt, the salt is prepared after removal of the R group or in situ during the deprotection reaction.

In step (c)(ii), the compound of formula IV is reacted with the free base or salt of formula I(c)(i) at elevated temperatures in an organic solvent such as acetonitrile, in the presence of a base such as $K_2CO_3$.

The optional recrystallization in step (d) of the product of step (b) or (c) is carried out using standard techniques, for example the crude product is dissolved in a heated organic solvent such as alcohol or an acetone/alcohol mixture, the resultant mixture is filtered, and then cooled (with seeding if necessary) to obtain the crystalline product.

Alkylation of the product of step (c), i.e. a compound of formula VI, to obtain a compound of formula V is achieved by methods well known in the art, for example by reaction of the product of step (c) with an alkyl iodide, e.g., methyl iodide, in the presence of a base.

The reactions of steps (a) to (d) are preferably carried out in an inert atmosphere, e.g., under nitrogen.

As used herein, "alkyl" means an aliphatic hydrocarbon group which may be straight or branched and comprising about 1 to about 6 carbon atoms in the chain. Branched means that one or more lower alkyl groups such as methyl, ethyl or propyl, are attached to a linear alkyl chain.

"Haloalkyl" means an alkyl groups as defined above substituted by 1-3 halogen atoms.

"Alkoxy" means an alkyl-O— group in which the alkyl group is as previously described. Non-limiting examples of suitable alkoxy groups include methoxy, ethoxy, n-propoxy, isopropoxy, n-butoxy and heptoxy. The bond to the parent moiety is through the ether oxygen.

"Aryl" means phenyl or naphthyl. $R^3$-aryl refers to such groups wherein substitutable ring carbon atoms have an $R^3$ substituent as defined above.

"Heteroaryl" means a single ring, bicyclic or benzofused heteroaromatic group of 5 to 10 atoms comprised of 2 to 9 carbon atoms and 1 to 4 heteroatoms independently selected from the group consisting of N, O and S, provided that the rings do not include adjacent oxygen and/or sulfur atoms. N-oxides of the ring nitrogens are also included. Examples of single-ring heteroaryl groups are pyridyl, oxazolyl, isoxazolyl, oxadiazolyl, furanyl, pyrrolyl, thienyl, imidazolyl, pyrazolyl, tetrazolyl, thiazolyl, isothiazolyl, thiadiazolyl, pyrazinyl, pyrimidyl, pyridazinyl and triazolyl. Examples of bicyclic heteroaryl groups are naphthyridyl (e.g., 1,5 or 1,7), imidazopyridyl, pyrido[2,3]imidazolyl, pyridopyrimidinyl and 7-azaindolyl. Examples of benzofused heteroaryl groups are indolyl, quinolyl, isoquinolyl, phthalazinyl, benzothienyl (i.e., thionaphthenyl), benzimidazolyl, benzofuranyl, benzoxazolyl and benzofurazanyl. All positional isomers are contemplated, e.g., 2-pyridyl, 3-pyridyl and 4-pyridyl. $R^3$-heteroaryl refers to such groups wherein substitutable ring carbon atoms have an $R^3$ substituent as defined above.

"Halogen" means a fluoro, chloro, bromo or iodo atom.

"Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

Certain compounds of the invention may exist in different stereoisomeric forms (e.g., enantiomers, diastereoisomers and atropisomers). The invention contemplates all such stereoisomers both in pure form and in mixture, including racemic mixtures.

Certain compounds will be acidic in nature, e.g. those compounds which possess a phenolic hydroxyl group. These compounds may form pharmaceutically acceptable salts. Examples of such salts may include sodium, potassium, calcium, aluminum, gold and silver salts. Also contemplated are salts formed with pharmaceutically acceptable amines such as ammonia, alkyl amines, hydroxyalkylamines, N-methylglucamine and the like.

Certain basic compounds also form pharmaceutically acceptable salts, e.g., acid addition salts. For example, pyrido-nitrogen atoms may form salts with strong acid, while compounds having basic substituents such as amino groups also form salts with weaker acids. Examples of suitable acids for salt formation are hydrochloric, sulfuric, phosphoric, acetic, citric, oxalic, malonic, salicylic, malic, fumaric, succinic, ascorbic, maleic, methanesulfonic and other mineral and carboxylic acids well known to those skilled in the art. The salts are prepared by contacting the free base form with a sufficient amount of the desired acid to produce a salt in the conventional manner. The free base forms may be regenerated by treating the salt with a suitable dilute aqueous base solution such as dilute aqueous NaOH, potassium carbonate, ammonia and sodium bicarbonate. The free base forms differ from their respective salt forms somewhat in certain physical properties, such as solubility in polar solvents, but the acid and base salts are otherwise equivalent to their respective free base forms for purposes of the invention.

All such acid and base salts are intended to be pharmaceutically acceptable salts within the scope of the invention and all acid and base salts are considered equivalent to the free forms of the corresponding compounds for purposes of the invention.

Following are descriptions of the preparation of compound I-A using the claimed process.

The following abbreviations, in addition to those defined above, are used in the specification and claims: Ms (methylsulfonyl); Me (methyl); ethyl acetate (EtOAc); LOD (loss on drying); DMAP (4-dimethylamino-pyridine); tert-butyl methyl ether (TBME); DMSO (dimethyl sulfoxide); gas chromatography (GC); and high performance liquid chromatography (HPLC).

Preparation 1

[Bis(2-chlorophenyl)methyl]amine hydrochloride

Step 1: Bis(2-chlorophenyl)methanol

Under $N_2$, 1-chloro-2-iodobenzene (40 ml, 0.33 mol) was dissolved in THF (360 ml) and cooled to −10 to −15° C. Within 30 min, a 1M solution of ethyl magnesium bromide (344 ml, 0.34 mol) in TBME was added at this temperature. The mixture was stirred at −10 to −15° C. and the reaction was followed by HPLC. After the reaction was complete (15 to 30 min), a solution of 2-chloro benzaldehyde (40.7 ml, 0.36 mol) in TBME (160 ml) was added at −10 to −15° C. within 30 min and the reaction was followed by HPLC. After complete reaction (15 to 30 min), the mixture was hydrolized with dilute HCl until all solids were dissolved at a final temperature of 20 to 25° C. The organic phase was washed with water (2×40 ml) and evaporated to dryness at a temperature of 45 to 50° C. The residue was co-evaporated twice with heptane (80 ml each) and crystallized from hot n-heptane (280 ml at 95 to 100° C.). The product was isolated by filtration after stirring for 1 h at 0 to 5° C. and washed with cold n-heptane (40 ml at 0 to 5° C.). The product was dried under vacuum at 50° C. to constant weight. Yield: 73.4 g (88%). Assay (HPLC): 100% pure vs. standard.

Step 2: 1,1'-(Bromomethylene)bis(2-chlorobenzene)

Under $N_2$, bis(2-chlorophenyl)methanol (70 g, 0.28 mol) was added in 4 portions at 20 to 25° C. to HBr (97 ml) in acetic acid (33% by weight). The mixture was stirred at 20 to 25° C. and the reaction was followed by HPLC. After complete reaction (60 to 90 min), the mixture was cooled to 0 to 10° C. and water (700 ml) was added over 30 min. The suspension was stirred at 0 to 10° C. for a further 30 min. The product was isolated by filtration and washed with water (4×140 ml). The product was dried under vacuum at 25° C. to constant weight. Yield: 82.6 g (95%). Assay (HPLC): 100% pure vs. standard Step 3: [Bis(2-chlorophenyl)methyl]amine hydrochloride Under $N_2$, 1,1'-(bromomethylene)bis(2-chlorobenzene) (110 g, 0.35 mol) was dissolved in $CH_3CN$ (550 ml) at 20 to 25° C. Over 30 min, gaseous ammonia (28.5 g, 1.7 mol) was passed into the solution at 20 to 25° C. (slight cooling is necessary). The mixture was heated in an autoclave to 93 to 96° C. for 3 h at a pressure of 6 bar. The mixture was stirred at 93 to 96° C. and the reaction was followed by HPLC. After complete reaction (10 to 14 h), the mixture was cooled to 20-25° C. and degassed. The suspension was concentrated under vacuum at 45 to 50° C. to a volume of 140 ml. Water (330 ml) was added and the mixture was concentrated again to a volume of 330 ml. To the residue, TBME (550 ml) was added and the phases were separated. The aqueous layer was extracted with TBME (110 ml). The combined organic phases were washed with water (110 ml, then 55 ml). The organic layer was evaporated to dryness at 45 to 50° C. and co-evaporated with ethanol (165 ml). Ethanol (330 ml) was added to the residue and the suspension was filtered after 30 min at 0 to 5° C. The solid was washed with ethanol (55 ml) and the combined filtrates were concentrated at 45 to 50° C. to a volume of 160 ml. The residue was added over 60 min to a mixture of water (960 ml) and conc. HCl (56 ml) at 0 to 5° C. The suspension was stirred for 2 h at 0 to 5° C. and filtered. The product was washed with 55 ml cold water (0 to 5° C.) and dried in vacuum at 50° C. to constant weight. Yield: 81.1 g (81%). Assay (HPLC): 100% pure vs. standard Preparation 2

2-Iodopyrimidine

Under $N_2$, 2-chloropyrimidine (200 g, 1.75 mol) was added in 5 portions to aqueous HI (850 ml, 57% in water) at −10 to −5° C. The mixture was stirred at −10 to −5° C. and the reaction was followed by HPLC. After complete reaction (60 to 120 min), the pH was set to 7.25±0.25 with NaOH (30%) and the temperature was increased to 18-23° C. To decolorize the mixture, 16 g $Na_2SO_3$ was added, decreasing the pH to 3±1. TBME (600 ml) was added to the mixture and the mixture was saturated with NaCl (300 g). The phases were separated and the aqueous phase was extracted with TBME (4×400 ml). The combined organic layers were washed with aqueous $Na_2SO_3$ (50 ml) (1%) and water (100 ml). The organic layer was evaporated to dryness and co-evaporated with TBME (100 ml) under vacuum at 45 to 50° C. Yield: 330 g (90%). Assay (HPLC): 98% pure vs. standard.

EXAMPLE 1

Embodiment 1

Step (a): 8-[Bis(2-chlorophenyl)methyl]-8-azabicyclo[3.2.1]octan-3-one

Under $N_2$, 2,5-dimethoxytetrahydrofuran (cis/trans) (51.6 ml, 0.40 mol) was added to a solution of conc. HCl (3.4 ml) in water (345 ml) at 20 to 25° C. The mixture was stirred at 20 to 25° C. and the reaction was followed by GC. After complete reaction (1 h), the mixture was cooled to 10 to 15° C. and sodium acetate trihydrate (141.4 g, 1.0 mol) and 1,3-acetone dicarboxylic acid (75.9 g, 0.52 mol) were added. After 5 to 10 min, a clear solution was obtained at 0 to 5° C. To this mixture, a solution of Preparation 1 (100 g, 0.35 mol) in NMP (840 ml) was added over 60 min at 3 to 7° C. The mixture was stirred at 0 to 5° C. for 60 min, during which evolution of $CO_2$ was observed. The mixture was slowly warmed up to 20 to 25° C. over 150 min and stirred at this temperature for an additional 75 min. The mixture was slowly heated to 50° C. over 90 min under increased evolution of $CO_2$ and stirred at 50° C. for another 90 min until $CO_2$ liberation finished. The mixture was cooled to 20-25° C. and was added over 20 min to well stirred ice water (4 l). The pH of the suspension was adjusted to 10-11 with NaOH solution (30%) and stirred for 60 min at 0 to 5° C. The product was filtered off and washed with water (2×250 ml). The product was dried under vacuum at 50° C. to constant weight (a slight stream of $N_2$ was applied). Yield: 117.3 g (70% abs.). Assay (HPLC): 75% pure vs. standard Purification:

Under $N_2$, crude product (150 g, 0.30 mol active) was dissolved in THF (300 ml) and isopropyl acetate (1500 ml) at 20 to 25° C. To the stirred solution, water (150 ml) was added and the pH was adjusted to 0.8±0.1 by the addition of 2N HCl. The mixture was stirred for 90 to 150 min at 20 to 25° C. The organic layer was separated and a solution of NaCl (30 g) in water (120 ml) was added under stirring. The pH of the mixture was adjusted to 11 with 2N NaOH solution and the mixture was stirred for 30 min. The phases are separated and the organic layer was washed with a mixture of water (120 ml) and saturated NaCl solution (30 ml). The organic layer was concentrated under vacuum at 50° C. to a volume of 375 ml and cooled to 0-5° C. over 100 min. The resultant suspension was stirred for 90 min at 0 to 5° C. The product was filtered off and washed with a cold (0 to 5° C.) mixture of heptane/isopropyl acetate 4:1 (2×75 ml). The product was dried under vacuum at 45 to 50° C. to constant weight. Yield: 88.4 g (80%). Assay (HPLC): 98% pure vs. standard.

Step (b): 8-[Bis(2-chlorophenyl)methyl]-3-pyrimidin-2-yl-8-azabicyclo[3.2.1]octan-3-ol Under $N_2$, LiBr (43.4 g, 0.50 mol) was added to a flask and heated to 130-140° C. under vacuum for 3 h. After cooling to 20-25° C., dry THF (500 ml) was added and the suspension was stirred at 20 to 35° C. until the salts were dissolved. This solution was added to a solution of the product of Step (a) (72 g, 0.20 mol) and 2-iodopyrimidine (Prep. 2) (61.5 g, 0.30 mol) in THF (550 ml). The mixture was cooled to −95±5° C. and n-butyl lithium (188 ml, 15% in n-hexane) was added over 30 min at this temperature. The mixture was stirred at −95±5° C. and the reaction was followed by HPLC. After complete reaction (20 to 30 min), the mixture was warmed up to −50 to −30° C. over 75 min and added over 10 min to a solution of $NH_4Cl$ in water (19.8 g in 290 ml) at 20 to 25° C. The mixture was warmed up to 20 to 25° C. and the phases were separated. The organic layer was washed with a solution of NaCl in water (23.2 g in 200 ml). The organic layer was concentrated under vacuum at 50° C. to a volume of 240 ml. To the resultant suspension, n-heptane (865 ml) was added, 400 ml were evaporated under vacuum at 50° C. and 400 ml n-heptane was added again. The suspension was cooled to 0 to 5° C. and stirred at this temperature for 60 min. The product was filtered off and washed with n-heptane (2×75 ml). The product was dried under vacuum at 50° C. to constant weight. Yield: 68.3 g (70% abs.). Assay (HPLC): 88% pure vs. standard.

Recrystallization:

Under $N_2$, the crude product (100 g, 0.18 mol active) was dissolved in acetone (250 ml) and isopropanol (1250 ml) under reflux. Charcoal and silica gel (5% each) were added, the mixture was refluxed for an additional 15 min and the suspension was filtered through a pad of celite. The filter cake was washed with warm isopropanol/acetone 5:1 (120 ml). The mixture was concentrated at normal pressure to 950 ml and seeded. The suspension was cooled over 2 h to 0-5° C. and stirred for an additional 60 min. The product was filtered off, washed with isopropanol (3×100 ml) and dried under vacuum at 50° C. to constant weight. Yield: 77.3 g (91% abs.). Assay (HPLC): 99.3% pure vs. standard.

EXAMPLE 2

Embodiment 2

Step (a): 8-Benzyl-8-azabicyclo[3.2.1]octan-3-one

Under $N_2$, a solution of benzylamine (36.1 ml, 0.33 mol) in water (435 ml) was added within 45 min at 3 to 8° C. to a solution of 1,4-butane dialdehyde (1.15 equiv.), 1,3-acetone dicarboxylic acid (1.5 equiv.) and sodium acetate trihydrate (2 equiv.) in 330 ml water as described in Example 1, Step (a). The mixture was warmed up to 50° C. over 5 h and kept at this temperature for 2 h. After cooling to 20-25° C., 80 ml conc. HCl was added and the solution was washed with TBME (2×240 ml). The pH of the aqueous phase was adjusted to 7-8 with NaOH and the product layer was separated. The aqueous phase was extracted with TBME (3× with a total of 240 ml). The combined product phases were dried over $Na_2SO_4$ and concentrated as completely as possible under vacuum at 50°. Yield: 68.7 g (90% abs.). Assay (HPLC): 93% pure vs. standard.

Step (b): 8-Benzyl-3-pyrimidin-2-yl-8-azabicyclo[3.2.1]octan-3-ol

The synthesis is done according to the procedure of Example 1, Step (b), starting with the crude product of Step (a) (110 g). After washing with brine, the product was isolated by evaporation of the organic phase in vacuum to dryness at 50° C. The residue was diluted with isopropanol (425 ml) and heated to reflux. After filtration, the solution is cooled to −15 to −10° C. and stirred for 60 min. The product is filtered off, washed with isopropanol (50 ml) and dried to constant weight under vacuum and a slight stream of $N_2$ at 50° C. Yield: 100 g (74%). Assay (HPLC): 100% pure vs. standard.

Step (c)(i): 3-Pyrimidin-2-yl-8-azabicyclo[3.2.1] octan-3-ol hydrochloride

Under $N_2$, the product of Step (b) (18.0 g, 61 mmol) was dissolved in 1,2-dichloroethane (180 ml) at 0 to 5° C. Over 5 min, 1-chloroethyl chloroformate (10 ml, 92 mmol) was added and the mixture was slowly warmed to 20-25° C. over 100 min. The mixture was then heated to 80-85° C. and the reaction was followed by HPLC. After complete reaction (2 to 4 h), the mixture was cooled to 50° C. and evaporated to dryness under vacuum. At 60 to 65° C., methanol (90 ml) was added and the mixture was stirred for 40 min until evolution of $CO_2$ ceased. The mixture was evaporated to dryness under vacuum at 50° C. To the residue, TBME (50 ml) was added and the mixture was stirred at 50° C. The suspension was cooled to 20-25° C. The product was filtered off, washed with TBME (2×30 ml) and dried under vacuum at 50° C. to constant weight. Yield: 15.8 g (81% abs.), hydrochloric acid salt. Assay (HPLC): 64% vs. free base (calc. 85%).

In an autoclave, 8-benzyl-3-pyrimidin-2-yl-8-azabicyclo[3.2.1]octan-3-ol (5.0 g, 17 mmol), palladium on charcoal (3,5 g, 5% Pd/C, 50% water wet) ethanol (27.5 ml) and 2N HCl (2.5 ml) were mixed and hydrogenated under a pressure of 0.5 to 1.5 bar at 50° C. The reaction was followed by HPLC. After complete reaction (6 to 8 h) the mixture was filtered and the residue washed with ethanol. The filtrate was concentrated to dryness under vacuum at 50° and the crude product is purified by column chromatography (90 g silica gel, methanol:ammonia (25%) 50:1). Yield: 1.8 g (52%) as free base. Assay (HPLC): 99% area.

Step (c)(ii): 8-[Bis(2-chlorophenyl)methyl]-3-pyrimidin-2-yl-8-azabicyclo[3.2.1]octan-3-ol Under $N_2$, a well stirred mixture of 3-pyrimidin-2-yl-8-azabicyclo[3.2.1]octan-3-ol hydrochloride (4.5 g, 14 mmol), 1,1'-(bromomethylene)bis(2-chlorobenzene) (5.0 g, 16 mmol) and $K_2CO_3$ (10.0 g, 72 mmol) in $CH_3CN$ (50 ml) was stirred under reflux and the reaction was followed by HPLC. After complete reaction (36 to 48 h) the mixture was cooled to 20-25° C., water (50 ml) was added and the suspension was stirred for 3 h. The product was filtered off, washed with water (2×25 ml) and dried to constant weight under vacuum and a slight stream of $N_2$ at 50° C. Yield: 5.5 g (87% abs.). Assay (HPLC): 97% pure vs. standard.

Step (d):

Under $N_2$, the crude product of Step (c) (4.9 g, 10.8 mmol) was dissolved in boiling isopropanol (100 ml). The hot mixture was filtered, cooled slowly to 0 to 5° C. and stirred for another 90 min. The product was filtered off, washed with isopropanol (10 ml) and dried under vacuum at 50° C. to constant weight. Yield: 4.4 g (93% abs.). Assay (HPLC): 99.8% pure vs. standard.

EXAMPLE 3

Embodiment 2

Step (a): 8-Allyl-8-azabicyclo[3.2.1]octan-3-one

The synthesis is done according to a procedure similar to that in Example 2, Step (a), starting from allylamine (25 ml) and sodium acetate trihydrate (3 equiv.). After cooling of the reaction mixture to 20-25° C., the pH was adjusted to 10 and the solution was extracted with EtOAc (4× with a total of 700 ml). The combined organic phases were dried over $Na_2SO_4$ and evaporated under vacuum at 50° C. to constant weight. Yield: 56 g (90% abs.). Assay (HPLC): 88% pure vs. standard.

Step (b): 8-Allyl-3-pyrimidin-2-yl-8-azabicyclo[3.2.1]octan-3-ol

The synthesis was done according to a procedure similar to that in Example 1, Step (b), starting from the crude product of Step (a) (50 g). After hydrolysis, the phases were separated and the aqueous layer was extracted with THF (4×330 ml). The combined organic layers were evaporated to dryness under vacuum at 50° C. and co-evaporated with THF (100 ml). The crude product was purified by column chromatography (1.2 kg silica gel, EtOAc:$Et_3$N=98:2). The residue obtained from the product fractions after evaporation under vacuum at 50° C. was crystallized from hexane (60 ml) at 40° C. After cooling to −15 to −10° C., the product was filtered off, washed with cold hexane (30 ml, at −15 to −10° C.) and dried in vacuum and a slight stream of $N_2$ at 35° C. to constant weight. Yield: 39.5 g (50% abs.). Assay (HPLC): 98% pure vs. standard.

Step (c)(i): 3-Pyrimidin-2-yl-8-azabicyclo[3.2.1] octan-3-ol

Under $N_2$, a solution of the product of Step (a) (4.0 g, 16 mmol) in $CH_3CN$ (40 ml) was added to N,N-dimethyl barbituric acid (5.1 g, 33 mmol) and tetrakis(triphenyl-phosphine) palladium (120 mg, 0.1 mmol) at 20 to 25° C. The mixture was stirred at 35 to 40° C. and the reaction was followed by HPLC. After complete reaction (30 min to 2 h), the mixture was cooled to 20-25° C. and stirred for another 60 min. The product was filtered off, washed with $CH_3CN$ (10 ml) and dried under vacuum at 50° C. to constant weight. Yield: 5.4 g (92%) as salt of N,N-dimethylbarbituric acid.

Step (c)(ii): 8-[Bis(2-chlorophenyl)methyl]-3-pyrimidin-2-yl-8-azabicyclo[3.2.1]octan-3-ol Using a procedure similar to that in Example 2, Step (c)(ii), with the product of Step (c)(i) (4.5 g, 12.5 mmol) as the starting material, the desired product was obtained. Yield: 5.2 g (90% abs.). Assay (HPLC): 95% pure vs. standard.

Step (d):

The recrystallization was done according to the procedure of Example 2, Step (d), on a 4.5 g scale. Additionally, the hot solution was treated with charcoal and silica gel (5% each). Yield: 3.6 g (83%). Assay (HPLC): 99.7% pure vs. standard.

While the present invention has been described in conjunction with the specific embodiments set forth above, many alternatives, modifications and variations thereof will be apparent to those of ordinary skill in the art. All such alternatives, modifications and variations are intended to fall within the spirit and scope of the present invention.

We claim:

1. A process for preparing a compound having the structural formula I

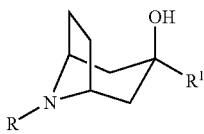

or a pharmaceutically acceptable salt thereof,
R is benzyl, -benzyl-$R^5$, allyl, —C(O)$R^6$, —C(O)O$R^8$ or —CH($R^7$)$_2$;
each $R^7$ is independently selected from the group consisting of -phenyl-$R^2$ or $R^2$-heteroaryl;
$R^1$ is $R^3$-aryl, $R^3$-heteroaryl, $R^3$-arylalkyl- or $R^3$-heteroarylalkyl-;
$R^2$ is 1 to 3 substituents independently selected from the group consisting of hydrogen, halogen, alkyl, hydroxy and alkoxy;
$R^3$ is 1-3 substituents independently selected from the group consisting of hydrogen, halogen and alkyl;
$R^5$ is 1 or 2 substituents independently selected from the group consisting of halogen, alkoxy and —NO$_2$;
$R^6$ is H, alkyl, haloalkyl or benzyl; and
$R^8$ is alkyl, benzyl or allyl;
comprising
a) reacting an amine of formula II

wherein R is as defined above, with 2,5-dimethoxytetrahydrofuran or HC(O)(CH$_2$)$_2$C(O)H, and with C(O)(CH$_2$C(O)O$R^4$)$_2$, wherein $R^4$ is H or alkyl, in a buffer, optionally in the presence of a base, to obtain a compound of formula III

b) reacting a compound of formula III with I-$R^1$, wherein $R^1$ is as defined above, with alkyl lithium, optionally in the presence of a lithium salt, to obtain a compound of formula I;

c) optionally converting a compound of formula I wherein R is benzyl, -benzyl-$R^5$, allyl, —C(O)$R^6$ or —C(O)O$R^8$ to a compound of formula I wherein R is —CH($R^7$)$_2$ by
i) reacting the compound of Formula III with a suitable reagent to remove the benzyl, -benzyl-$R^5$, allyl, —C(O)$R^6$ or —C(O)O$R^8$ group to obtain a compound of formula I(c)(i)

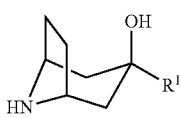

and
ii) reacting the compound of I(c)(i) or a salt thereof with a compound of formula IV

CH($R^7$)$_2$—X   IV wherein X is halogen, —OSO$_2$CH$_3$ or —O-(p-toluenesulfonyl) thereby yielding the compound of formula I wherein R is —CH($R^7$)$_2$; and d) optionally recrystallizing the product of step b) or step c) to obtain a purified product.

2. The process of claim 1 wherein R is

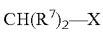

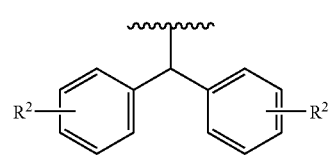

wherein each $R^2$ is halogen.

3. The process of claim 2 wherein each $R^2$ is 2-chloro.
4. The process of claim 1 wherein $R^1$ is $R^3$-heteroaryl.
5. The process of claim 4 wherein $R^3$-heteroaryl is 2-pyrimidyl.
6. The process of claim 1 for preparing the compound of formula Ia

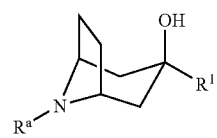

wherein $R^a$ is —CH($R^7$)$_2$ and $R^1$ is $R^3$-aryl, $R^3$-heteroaryl-, $R^3$-arylalkyl- or $R^3$-heteroarylalkyl-, comprising:
a) reacting an amine of formula IIa CH($R^7$)$_2$—NH$_2$   IIa with 2,5-dimethoxy-tetrahydrofuran or HC(O)(CH$_2$)$_2$C(O)H, and C(O)(CH$_2$C(O)O$R^4$)$_2$, wherein $R^4$ is H or alkyl, in a buffer, optionally in the presence of a base, to obtain a compound of formula IIIa

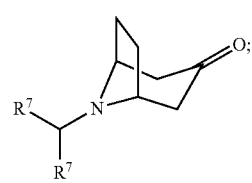

b) reacting a compound of formula IIIa with I-$R^1$, wherein $R^1$ is as defined above, with alkyl lithium, optionally in the presence of a lithium salt, to obtain a compound of formula Ia; and optionally recrystallizing the product of step b) to obtain a purified product.

7. The process of claim 6 wherein in step (a), the amine of formula IIa is

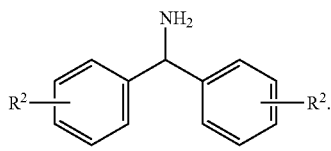

8. The process of claim 6 for preparing the compound of formula Ia'

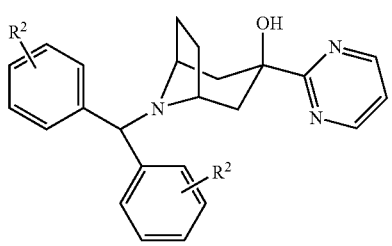

wherein $R^2$ is 1 to 3 substituents independently selected from the group consisting of hydrogen, halogen, alkyl, hydroxy and alkoxy;

comprising a) reacting an amine of the formula IIa'

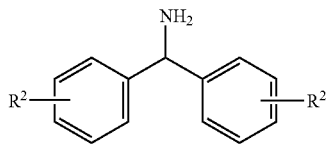

with 2,5-dimethoxytetrahydrofuran and $C(O)(CH_2C(O)OR^4)_2$, wherein $R^4$ is H, in a buffer, optionally in the presence of a base, to obtain a compound of formula IIIa'

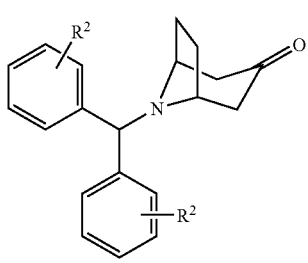

b) reacting a compound of formula IIIa' with 2-iodopyrimidine, LiBr and n-butyl lithium to obtain a compound of formula Ia'; and optionally recrystallizing the product of step b) to obtain a purified product.

9. The process of claim 1 for preparing the compound of formula Ia

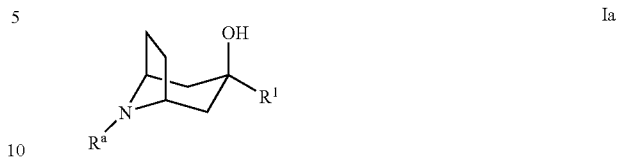

wherein $R^a$ is $-CH(R^7)_2$ and $R^1$ is $R^3$-aryl, $R^3$-heteroaryl, $R^3$-arylalkyl- or $R^3$-heteroarylalkyl-;

comprising a) reacting an amine of formula IIb

wherein $R^b$ is benzyl, -benzyl-$R^5$, allyl, $-C(O)R^6$ or $-C(O)OR^8$, with 2,5-dimethoxy-tetrahydrofuran or $HC(O)(CH_2)_2C(O)H$, and $C(O)(CH_2C(O)OR^4)_2$, wherein $R^4$ is H or alkyl, in a buffer, optionally in the presence of a base, to obtain a compound of formula IIIb

b) reacting a compound of formula IIIb with I-$R^1$, wherein $R^1$ is as defined above, with alkyl lithium, optionally in the presence of a lithium salt, to obtain a compound of formula Ib

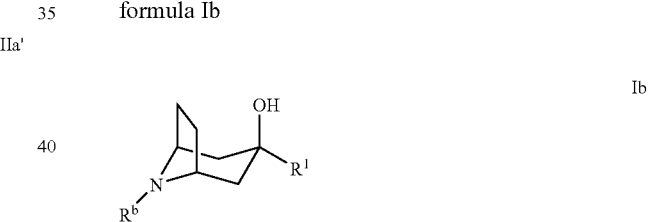

wherein $R^b$ is as defined above;

c) converting the compound of formula Ib to a compound of formula Ia wherein $R^a$ is $-CH(R^7)_2$ by:
  i) reacting the compound of Formula III with a suitable reagent to remove the benzyl, -benzyl-$R^5$, allyl, $-C(O)R^6$ or $-C(O)OR^8$ group to obtain a compound of formula I(c)(i)

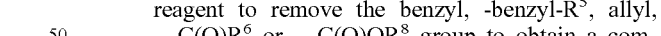

and
  ii) reacting the compound of formula I(c)(i) or a salt thereof with a compound of formula IV $$CH(R^7)_2-X \qquad \text{IV}$$

wherein X is halogen, $-OSO_2CH_3$ or $-O$-(p-toluenesulfonyl) thereby yielding the compound of formula I wherein R is $-CH(R^7)_2$; and d) optionally recrystallizing the product of step c) to obtain a purified product.

10. The process of claim 9 for preparing a compound of formula Ia'

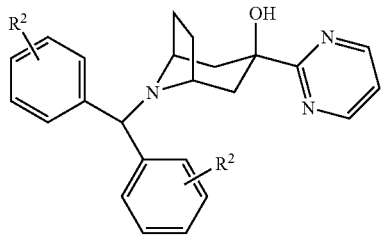

Ia' wherein $R^2$ is 1-3 substituents independently selected from the group consisting of hydrogen, halogen, alkyl, hydroxy and alkoxy;

comprising a) reacting an amine of formula IIb $R^b$—$NH_2$   IIb wherein $R^b$ is benzyl, -benzyl-$R^5$, allyl, —C(O)$R^6$ or —C(O)O$R^8$, with 2,5-dimethoxy-tetrahydrofuran or HC(O)(CH$_2$)$_2$C(O)H, and C(O)(CH$_2$C(O)O$R^4$)$_2$, wherein $R^4$ is H or alkyl, in a buffer, optionally in the presence of a base to obtain a compound of formula IIIb

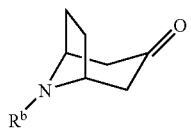

IIIb b) reacting a compound of formula IIIb with 2-iodopyrimidine, LiBr and n-butyl lithium to obtain a compound of formula Ib"

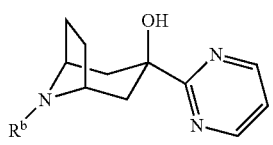

Ib"

wherein $R^b$ is as defined above;

c) converting the compound of formula Ib" to a compound of formula Ia' wherein $R^a$ is

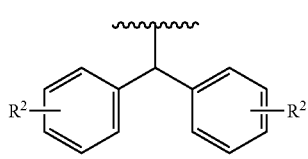

by i) removing the benzyl, -benzyl-$R^5$, allyl, —C(O)$R^6$ or —C(O)O$R^8$ group to obtain a compound of formula I(c)(i)'

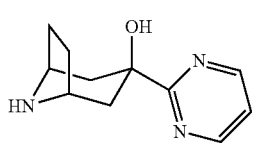

I(c)(i)' ii) reacting the compound of formula I(c)(i)' or a salt thereof with a compound of formula IV'

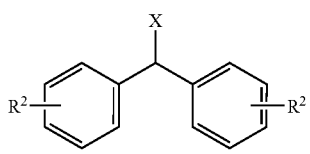

IV' wherein X is halogen, —OSO$_2$CH$_3$ or —O-(p-toluenesulfonyl); and d) optionally recrystallizing the product of step c) to obtain a purified product.

11. A compound of the formula

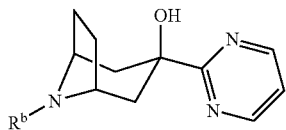

wherein $R^b$ is benzyl, -benzyl-$R^5$, allyl, —C(O)$R^6$ or —C(O)O$R^8$ wherein $R^5$ is 1 or 2 substituents independently selected from the group consisting of halogen, alkoxy and —NO$_2$;

$R^6$ is H, alkyl, haloalkyl or benzyl; and $R^8$ is alkyl, benzyl or allyl.

12. A compound of the formula

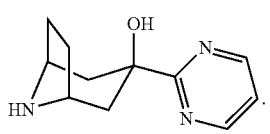

13. A process for preparing a compound of formula V

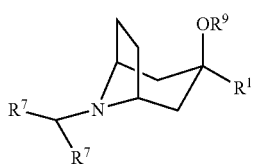

V wherein
- $R^1$ is $R^3$-aryl, $R^3$-heteroaryl, $R^3$-arylalkyl- or $R^3$-heteroarylalkyl-;
- $R^3$ is 1-3 substituents independently selected from the group consisting of hydrogen, halogen and alkyl;
- each $R^7$ is independently selected from the group consisting of -phenyl-$R^2$ or $R^2$-heteroaryl;
- $R^2$ is 1 to 3 substituents independently selected from the group consisting of hydrogen, halogen, alkyl and alkoxy; and
- $R^9$ is alkyl;

comprising alkylating a compound of the formula VI

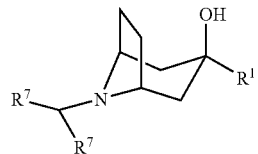

VI.

* * * * *